United States Patent [19]

Wilson

[11] Patent Number: 4,808,159
[45] Date of Patent: Feb. 28, 1989

[54] APPARATUS AND METHOD FOR ADMIXTURE BLOOD WARMING

[75] Inventor: Ethan B. Wilson, Tucson, Ariz.

[73] Assignee: Minnesota Mining and Manufacturing Company, St. Paul, Minn.

[21] Appl. No.: 26,478

[22] Filed: Mar. 16, 1987

[51] Int. Cl.$^4$ .............................................. A61M 37/00
[52] U.S. Cl. ......................................... 604/4; 604/113
[58] Field of Search .................. 604/113, 114, 56, 51, 604/49, 403, 408, 410, 4–6, 80–86

[56] References Cited

U.S. PATENT DOCUMENTS

| 771,600 | 10/1904 | Bauer. | |
|---|---|---|---|
| 1,161,401 | 11/1915 | Meinecke. | |
| 2,396,043 | 3/1943 | Evans. | |
| 2,910,981 | 11/1959 | Wilson et al. | |
| 3,044,465 | 7/1962 | Anderson et al. | |
| 3,572,338 | 0/1971 | Murray, Jr. | 128/229 |
| 4,249,923 | 2/1979 | Walda | 62/394 |
| 4,416,280 | 11/1983 | Carpenter et al. | 128/399 |
| 4,430,078 | 2/1984 | Sprague | 604/141 |
| 4,531,941 | 7/1985 | Zasuwa | 604/113 |
| 4,539,005 | 9/1985 | Greenblatt | 604/141 |
| 4,623,333 | 11/1986 | Fried | 604/80 |
| 4,678,460 | 7/1987 | Rosner | 604/113 |
| 4,705,508 | 11/1987 | Karnavas et al. | 604/4 X |

Primary Examiner—John D. Yasko
Attorney, Agent, or Firm—Donald M. Sell; Robert W. Hoke, II

[57] ABSTRACT

Rapid mechanical admixing of blood products at a storage temperature of 4° C. with a saline solution in a temperature range of 50°–70° C. results in a mixture temperature sufficient to prevent hypothermia upon transfusion, which temperature rise per volume of the blood products is at a rate commensurate with the flow rate of transfusion equipment while not exceeding the temperature tolerance of the erythrocytes.

38 Claims, 2 Drawing Sheets 4,808,159

APPARATUS AND METHOD FOR ADMIXTURE BLOOD WARMING

BACKGROUND OF THE INVENTION

1. Field of the Invention

The present invention relates to blood warming apparatus and, more particularly, to apparatus for mechanically and rapidly admixing blood products at a storage temperature with a heated saline solution to produce a transfusable mixture without significant hemolysis at a rate commensurate with transfusion equipment and at a temperature within an acceptable range to avoid hypothermia.

2. Related Prior Art

The management of massive blood loss resulting from trauma or surgery necessitates rapid transfusion capability. In order to avoid the deleterious effects of hypothermia, it is necessary to warm blood from it's normal storage temperature of approximately 4° C. prior to transfusion. Currently accepted blood warmers utilize passive heat transfer via dry warming panels or coils in a water bath. These warmers cannot adequately warm blood at flow gates exceeding 500 ml/minute. This slow warming rate represents the rate-limiting step in rapid transfusion. Other methods of blood warming which have been suggested include microwave ovens, which are considered to cause unacceptable hemolysis; blood bag emersion which is slow and not completely clinically tested; and, an extracorporeal heat exchanger which utilizes expensive equipment and has not been completely clinically studied.

Erythrocyte incubation studies have shown that prolonged exposure to temperatures greater than 48° C. results in hemolysis and increased erythrocyte osmotic fragility. These results have been applied to the design of currently available blood warmers. Accordingly, heat source temperatures below 40° C. are used which results in a slow transference of heat and dictates maximal blood warmer flow rates of less than 500 ml/minute. Because of these relatively low flow rates, blood warmer use in the emergent setting is often stopped just when a patient's transfusion requirement increases to the point where warming becomes most valuable. A typical state of the art blood warmer is sold under the trademark "INFUSER 37" by C. R. Bard, Inc. of Billerica, Mass. This blood warmer requires a heat exchanger wherein the heating water temperature is 40° C. at a minimum flow rate of 10 l/minute.

SUMMARY OF THE INVENTION

The apparatus for warming includes a container for blood products retrieved from cold storage and at a temperature of 4°-10° C. Apparatus for rapidly discharging the blood product from it's container is associated with the container. The apparatus also supports a further container for a saline solution at a temperature in the range of 50° C. to less than 80° C. Apparatus for rapidly evacuating the saline solution from it's container is associated with the container. A conduit extends from each of the blood products container and the saline solution container to a junction wherefrom a further conduit conveys a mixture of the fluids to transfusion related equipment. The saline solution can be expressed from its container through the conduit into the blood products container. Apparatus acting upon the blood products container during inflow of the saline solution will force rapid mechanical admixing with the blood products. The resulting mixture, being at a temperature within the range suitable for transfusion and without hemolysis due to the rapid mixing, may be injected through conventional transfusion apparatus. In the alternative, the contents of the two containers can be expressed simultaneously. A rapid admixing of the blood products and the saline solution will occur due to the intersection of the two resulting streams of fluid at the junction of the conduits. The admixing will raise the temperature of the mixture to a range sufficient to prevent hypothermia and without causing hemolysis.

It is therefore a primary object of the present invention to provide rapid mechanical mixing of chilled blood products with a heated saline solution for transfusion without danger of hypothermia or hemolysis.

Another object of the present invention is to provide apparatus for rapidly warming blood products to a temperature suitable for transfusion without danger of hypothermia.

Still another object of the present invention is to provide apparatus for rapidly warming erythrocytes without creating a danger of hemolysis.

Still another object of the present invention is to provide apparatus for warming blood products commensurate with the flow rate of available transfusion equipment.

A further object of the present invention is to provide a method for rapidly warming erythrocytes A yet further object of the present invention is to provide a method for admixing chilled blood products and heated saline solution at a rate commensurate with transfusion equipment without danger of hemolysis.

A still further object of the present invention is to provide a method for mechanically mixing blood products with a heated saline solution to rapidly raise the temperature of the blood products.

These and other objects of the present invention will become apparent to those skilled in the art as the description thereof proceeds.

BRIEF DESCRIPTION OF THE DRAWINGS

The present invention may be described with greater clarity and specificity with reference to the drawings, in which.

DESCRIPTION OF THE PREFERRED EMBODIMENT

Figure 1:
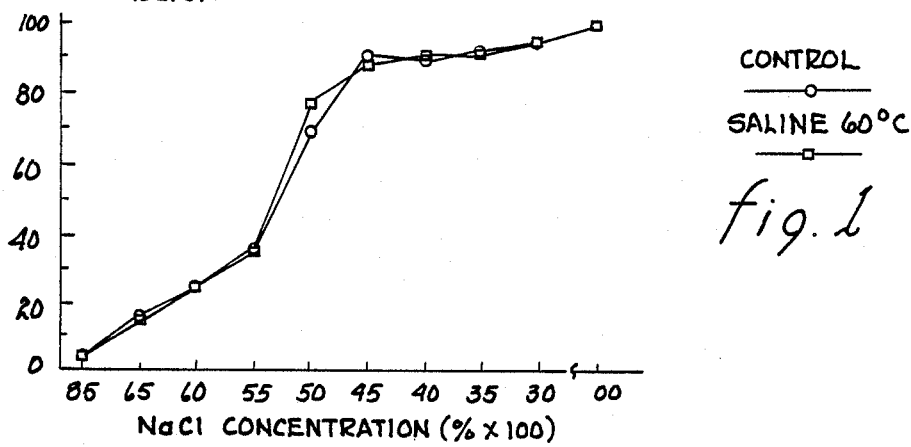
FIGS. 1–3 are graphs depicting osmotic fragility.

The need for rapid transfusion arises frequently in emergency departments, at surgery and at critical care units. Prior to transfusion, however, blood products are stored at 4° C. and require warming to avoid lowering core temperature. The cardiac dysrhythmia resulting from transfusion induced hypothermia have been well documented. For this reason, various methods of blood warming have been developed utilizing external heat sources such as water baths, metal warming plates or microwave ovens. Problems arising from these blood warmers include slow flow rates, bulky and inconvenient equipment and damage to erythrocytes. As a result of these difficulties, especially because of low flow rates, blood warmer use in the emergent setting is often suspended as the urgency of the patient's transfusion requirement increases. This disuse of blood warmers allows for the infusion of blood products at temperatures much below that which would be considered safe.

Erythrocyte incubation studies show that prolonged (greater than 15 minutes) exposure to temperatures over 45° C. result in significant hemolysis. For this reason, commercial blood warmers utilize heat source temperatures below 40° C. This low temperature source tends to limit maximal blood warmer flow rates to 500 ml/minute or less due to the time needed for sufficient heat transference. When compared with available flow rates of over 1200 ml/minute for pressurized intravenous fluid administration sets incorporating large bore catheters, it becomes obvious that blood warmers represent a very significant rate limiting step in transfusion therapy.

One step common to all methods of blood warming for rapid transfusion is the dilution of erythrocytes prior to transfusion. This is necessary in order to optimize flow rates, given the high viscosity of undiluted erythrocytes. Admixture blood warming expands the utility of this process by combining dilution and warming into one step. It results in warmed erythrocytes with a hematocrit equal to that of whole blood.

The gist of the present invention which represents a major departure from previous blood warming apparatus and research is the concept that erythrocytes tolerate rapid admixture with a saline solution at temperatures in excess of 45° C. This is true despite the fact that the erythrocytes do not tolerate prolonged incubation at temperatures exceeding 45° C. The admixture process, with it's rapid equilibration at an intermediate temperature, does not result in prolonged erythrocyte exposure to elevated temperatures. As a result, the erythrocytes can be rapidly warmed without hemolyzing.

To verify this hypothesis, an experiment was conceived and the results analyzed. In the experiment, plasma hemoglobin concentrations were utilized as an indicator of erythrocyte trauma. The concentrations reflect the release of hemoglobin following erythrocyte membrane disruption. Plasma hemoglobin, also called free hemoglobin, has been utilized for this purpose in most blood warming studies. These studies have presumed, and clinical experience in blood transfusion has supported, the concept that the most labile component of an erythrocyte is it's membrane rather than the hemoglobin. Presumably, if the erythrocyte membrane integrity is maintained, then the enclosed hemoglobin will be functional.

Comparing admixture blood warming with studies of other blood warming methods reveals similar levels of plasma hemoglobin in warmed samples. In no instance did plasma hemoglobin levels rise to a clinically important level, that is, to a level greater than that which could be cleared by the haptoglobinlymphoreticular system. Adults are able to clear up to five grams of free hemoglobin before beginning to develop hemoglobinuria. This is obviously greater than the approximate 600 mg of plasma hemoglobin (per unit transfused blood) which would be present if one assumed hemolysis at the highest rate in the 70° C. saline admixture using 35 day old erythrocytes.

Clinical application of blood warming with the present invention would require the availability of heated containers of normal saline solution. Methods for heating saline solution containers include microwave ovens or dry oven/incubator. While use of microwave ovens to warm saline solution is an acceptable method, it introduces an additional time delay prior to beginning transfusion. Owing to changes in saline concentration over time, long term water bath incubation is not recommended by at least certain of the manufacturers of the saline solution. Blanket warmers to not offer close enough temperature regulation $(+/-5.5°$ C.) to be acceptable for application. At present, the most acceptable instrument for saline solution heating and storage is a microbiological incubator. This type of unit provides close temperature regulation $(+/-0.5°$ C.) and is able to achieve the temperatures utilized herein.

The materials for admixture blood warming are already used in transfusion therapy. These include saline solution bags, large bore transfusion sets, Y-type transfusion sets and plasma transfer sets. For transfer of the saline solution during the admixture process, pressure can be applied by hand or by using a standard pressure cuff. Optimal control of the mixture temperature will be obtained by ensuring a 1:1 saline/erythrocyte mixture. This may necessitate either standardization of erythrocyte volumes or weighing of individual units and admixing with an equal amount of heated saline solution. Assessment of mixture temperature can be achieved using external temperature sensors.

Testing, as described in further detail below, was performed to determine the effect of admixture using a saline solution at temperatures of 60° C., 70° C. and 80° C. These tests evaluated subtle membrane effects as assessed by erythrocyte osmotic fragility testing.

Units of red blood cells were prepared from blood collected in citrate-phosphate-dextrose-adenine solution (CPDA-1) and stored in standard blood containers at 4° C. until used. The average hematocrit of these units was 75%. At the time of the admixture tests, the units were divided into paired aliquotes of 100 to 125 g. each. All admixture tests and controls were done on day 35 following blood donation. For admixture tests, saline solution bags (such as travenol 0.9% NaCl)) were weighted to within one gram of the erythrocyte aliquotes (100 to 125 g.). The saline solution bags were then water bath heated to either 60°,70° or 80° C. Temperature was determined using an in-bag probe (such as Hewlett-Packard #2802A). Bags of erythrocytes, at 6°-10° C. were gently agitated by hand while heated saline was rapidly added under hand-generated pressure via a plasma transfer set. This was accomplished by squeezing the saline solution bag with a gloved hand. Agitation consisted of a rapid (once per second) rocking of the blood bag. Saline was transferred within 15 seconds agitation continued for 1 minute. The mixture temperature was measured by a probe in the bag and samples were obtained for osmotic fragility tests. The mixture was then centrifuged and the resultant supernatant assessed for plasma hemoglobin. Five trial were carried out at each temperature with a control for each trial and a total of 15 units of blood were used.

The controls consisted of an in-bag admixture of 100–125 g. aliquotes of erythrocytes (at 6°-10° C.) with an equal amount of cold saline (at 6°-10° C.). Osmotic fragility of the resultant mixture was determined utilizing incubation in ten concentrations of NaCl (0–0.85%) followed by centrifugation (1000 g for 10 minutes) and colormetric reading at 540 nm. Plasma hemoglobin concentrations were determined following centrifugation of the admixture product (1000 g for 10 minutes). Colormetric absorption of the supernatant was assessed at 560, 575 and 590 nm. The technique was standardized using known concentrations of hemoglobin.

The mean temperatures of the resultant erythrocyte-saline mixtures for the five trials at each of the saline temperatures (60°, 70° and 80° C.) were 30.9°, 37.5° and 42.6° C., respectively.

Table 1 below shows the plasma hemoglobin and potassium values for control and admixture trials.

TABLE 1

| Saline Temp (°C.) | n | Plasma Hgb (mg %) | | Potassium (meq/l) | |
|---|---|---|---|---|---|
| | | control | trial | control | trial |
| 60 | 5 | 282.0 | 242.1* | 16.6 | 16.2* |
| 70 | 5 | 184.7 | 158.7* | 11.7 | 10.6* |
| 80 | 5 | 131.3 | 1244.0** | 12.2 | 14.4** |

**significant increase over control (p < .01)
*no significant increase over control values No significant elevation of plasma hemoglobin or potassium occurred in trials utilizing 60°-70° C. saline. Admixture with 80° C. saline solution resulted in significant elevation of plasma hemoglobin and potassium ($p < 0.01$, paired t-test).

Figure 2:
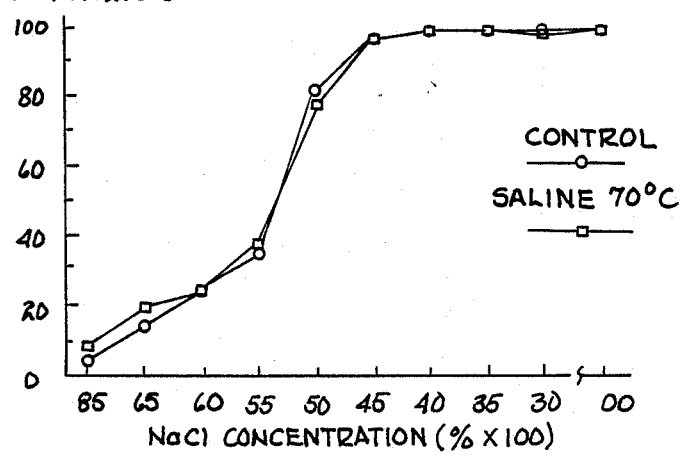
Figure 3:
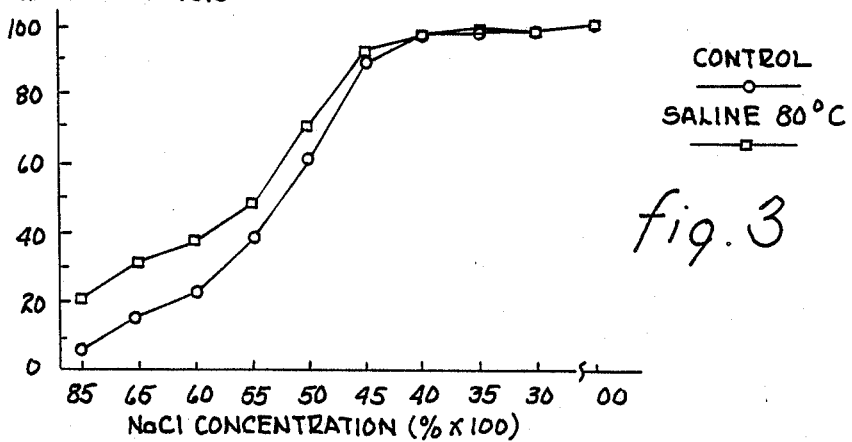

FIGS. 1 to 3 show average osmotic fragility curves for controls and admixture trials at each of the three saline solution temperatures. No significant difference was found between control and trials at any concentration of NaCl (0–0.85%) for saline solution temperatures of 60° C. and 70° C. Trials using 80° saline solution resulted in significantly increased osmotic fragility at multiple levels of NaCl concentration ($p < 0.01$, paired t-test).

Figure 4:
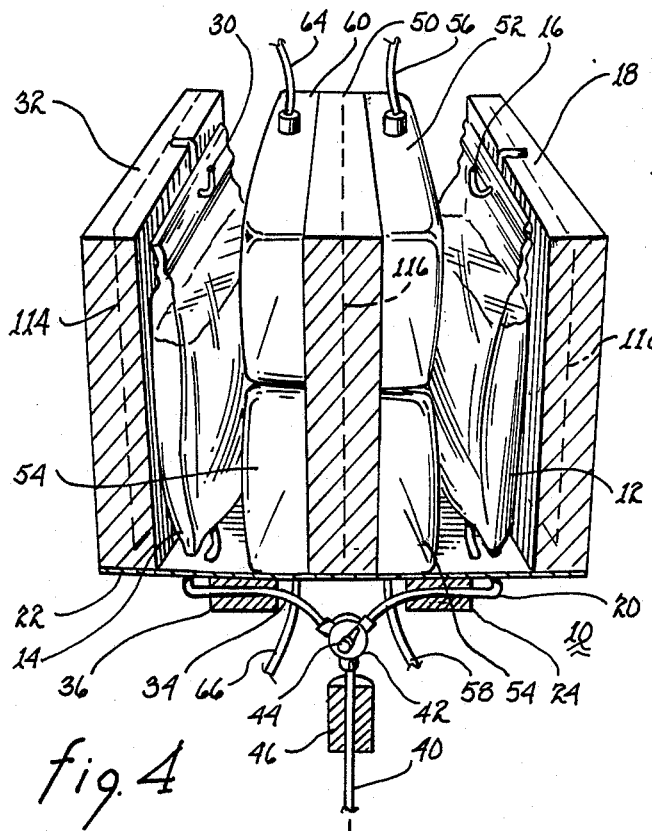
FIG. 4, is a perspective view of an embodiment of the present invention.

Turning now to FIG. 4, there is shown a blood warmer device 10 for effecting a rapid mechanical mixing of blood products in a container 12 at storage temperature (4° C.) with a heated saline solution in container 14. As used herein, the term blood products is intended to include whole blood, packed cells, erythrocytes, hemoglobin solutions, synthesized alterations of hemoglobin or blood substitutes. Container 12 may be of the standard bag type used in the industry for collecting and storing erythrocytes (red blood cells). It may be suspended from a suitably configured hook 16 supported by sidewall 18. The container includes a discharge tube 20 extending from the lower end in penetrable engagement with a base 22. Flow control means 24 regulates the flow through tube 20. Container 14 may be an industry standard bag type for saline solution. Container 14 is suspended by a hook 30 supported by sidewall 32. Container 14 also includes a tube 34 for discharging fluid out of the container and flow control means 36 regulates the flow through the tube.

A discharge conduit 40 is in fluid communication with tubes 20, 34 through a multi-port valve 42, which valve can accommodate flow between tubes 20 and 34 or between tube 34 and conduit 40 through manipulation of a pointer/knob 44, which may be substituted by semi-automatic or automatic flow control/regulation devices. A flow control means 46 regulates flow through conduit 40. It is to be understood that any or all of flow control means 24, 36 and 46 may include any type of functionally related devices, such as centrifugal or roller pump assemblies for drawing or forcing fluid flow.

A partition 50 extends upwardly from base 22 for supporting means for expressing fluid from container 14 and for independently or simultaneously expressing fluid from container 12. Means for rapidly mechanically agitating the contents of container 12 may also be supported upon partition 50. In the embodiment illustrated, air bags, such as air bags 52, 54, are supported upon partition 50 adjacent container 12. A source of air under pressure, including pressure regulating means, (not illustrated) is connected to inlet conduit 56 of air bag 52 and inlet conduit 58 of air bag 54. Upon inflation of either or both of air bags 52, 54, they will expand to bear against container 12 and urge evacuation of container 12 commensurate with the air bag pressure and degree of flow restriction presented by flow control means 24 and discharge tube 20. Control means, not illustrated, may be employed to sequentially inflate/deflate air bags 52, 54 to urge rapid movement of the liquid within container 12 in response to the alternating locations of application of pressure.

Partition 50 may also be employed to support a pair of air bags 60, 62 adjacent container 14. A source of air pressure and pressure regulating means (not illustrated) may be employed to regulate air flow into and out of the air bags through inlet conduits 64, 66. Expansion through inflation of either or both air bags 60, 62 will exert pressure against container 14 to urge expressing of any fluid contained therein through tube 34. If air bags 60, 62 are alternatively inflated/deflated, the resulting alternating pressure forces acting upon container 14 will have the effect of repetitively relocating the fluid within container 14. Such relocation will agitate the fluid and produce rapid mixing if the fluid is not already homogenous in content or temperature.

Figure 5:
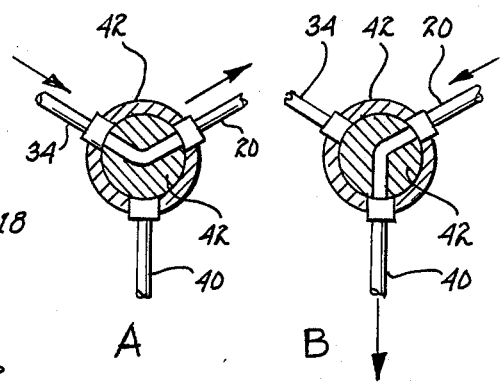
FIGS. 5a and 5b illustrate flow directions during each of two phases of operation of the present invention.

Referring jointly to FIGS. 4, 5a, 5b and 6, the operation of blood warmer device 10 will be described. Container 14, containing heated saline solution to be mixed with blood products and to be infused by transfusion and at a temperature in the range of 50° to less than 80° C., is suspended from hook 30 adjacent sidewall 32. Container 12, containing blood products to be infused by transfusion and at a temperature of approximately 4° C., is suspended from hook 16 adjacent sidewall 18. Upon inflation of air bags 60, 62, pressure will be brought to bear against container 14 to express the contents thereof. Upon opening (operation) of flow control means 36, the saline solution will flow through tube 34 to multi port valve 42, as indicated by the arrow in FIG. 5a. Assuming that knob 44 has been actuated to interconnect tube 34 with tube 20, as depicted in FIG. 5a and that flow control means 46 is closed, the saline solution will flow through valve 42, tube 20 and into container 12. Simultaneously, air bags 52 and 54 may be inflated/deflated alternately to exert, at alternate locations, pressure upon container 12. Such induced alternating pressure forces at different locations will result in mechanically forcing any fluid within container 14 to be rapidly agitated. Thereby, the saline solution flowing into container 12 through tube 20 is rapidly admixed with the blood products. Upon evacuation of container 14, the admixing within container 14 may continue for a period of time or may be terminated.

The admixture in container 14 is discharged therefrom through tube 20 and multi port valve 42 after knob 40 has been turned to provide flow into conduit 40, as depicted in FIG. 5b. The flow through conduit 40 may be regulated by flow control means 46. From conduit 40, the admixture flows to and is injected by conventional transfusion equipment.

From the above-description, it will be evident that air bags 52, 54 impose mechanical forces upon container 14 to agitate rapidly any fluid within the container, which agitation results in mixing of any fluids therein. The degree of force to be applied and hence severity of agitation is a function of the pressures exerted by the air bags.

Rapid mechanical mixing ma also be effected by the present invention through multi port valve 42. In the configuration of valve 42 depicted in FIG. 6, flow from each of tubes 20, 34 into conduit 40 is possible. At intersection 70 of the flows, particularly if the flow rates are significant, an admixing of the fluids will occur. Through such admixing, a temperature equilibrium of the admixture will come about relatively rapidly upon flow of the admixture into conduit 40. The force exerted by the fluids upon one another at intersection 70 will be a function of the completeness of the admixture. It will be immediately apparent that the admixture which occurs at intersection 70 will be sufficiently brief to preclude incubation of any blood products at a temperature higher than 45° C. for any significant time period if the initial temperature of the blood products is 4°-10° C. and the temperature of the saline solution is 50° C. to less than 80° C. it is to be understood that the above described function of intersection 70 could be accomplished by a mixing chamber of simple or complex design and capability.

Figure 7:
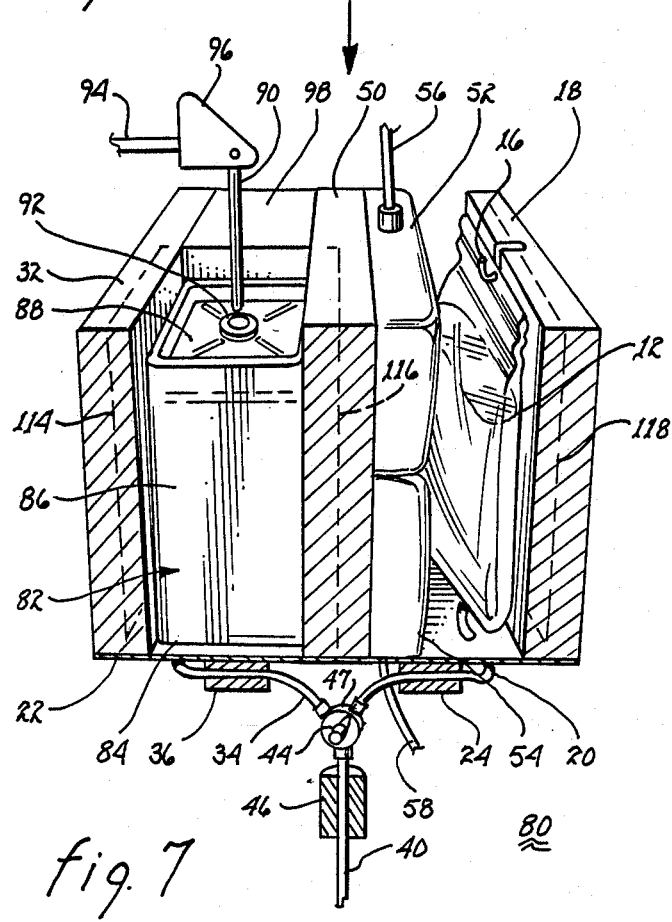
FIG. 7 is a perspective view of a variant of the present invention.
Figure 6:
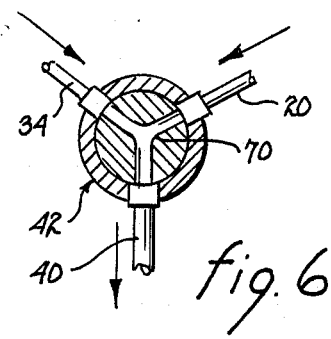
FIG. 6 illustrates the flow direction during a further operation of the present invention.

FIG. 7 illustrates a variant 80 of blood warmer device 10 illustrated in FIG. 4. To the extent the device shown in FIG. 7 is equivalent to the device shown in FIG. 4, the same reference numerals will be employed. The flexible container for saline solution shown in FIG. 4 has been replaced with a rigid sleeve and piston unit 82. A bottom 84 extends across sleeve 86 to develop a container for retaining a fluid, such as a saline solution to be expressed. Conduit 34 extends into bottom 84 and is in fluid communication with the contents of the unit. A translatable piston 88 is actuatable by a connecting rod or plunger 90 bearing against a receiving cup 92. A plurality of linkages and pivot mechanisms, as depicted by numerals 94, 96, respectively, provide rectilinear translation to the plunger. Although not so depicted in FIG. 7, it is to be understood that closed compartment 98 may be employed to house motive means for translating plunger 90 through linkages 94, 96. Other means for imparting translatory movement to piston 88 may also be employed.

Figure 8:
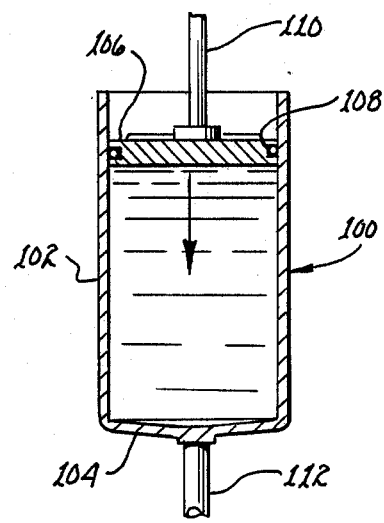
FIG. 8 is a partial view of a variant for expressing a fluid.

The sleeve and piston unit depicted in FIG. 7 illustrates the unit to be essentially rectangular in cross section. Under certain circumstances, such configuration may not be preferred. Accordingly, a more conventional cylindrical sleeve and piston unit 100 is depicted in FIG. 8. Herein, sleeve 102 is terminated at its lower end by a bottom 104 having tube 112 connected thereto to convey a fluid expressed from the unit. A disc like piston 106 is in sealed engagement with the interior surface with sleeve 102 through O-ring 108, or the like. A rod 110, connected to a source of power (not illustrated) imparts a downward force upon the piston, which downward force discharges the fluid from within the compartment defined by piston 106 and sleeve 102 through tube 112. It is to be understood that sidewall 32 and partition 50 (see FIG. 7) can be modified to receive and retain unit 100 and that the latter is capable of functioning in the manner of unit 82. It is to be understood that collapsible bags of saline solution can be placed within either of units 82, 100 to be expressed by force of the respective piston; means must be adapted to place discharge tube 34 in fluid communication with the bag.

If a saline solution is housed as shown in FIG. 4 or in either of sleeve and piston units 82, 100, sidewall 32 and partition 50 may be adapted to support heating elements for warming or for maintaining the temperature of the saline solution within the respective container. These heating units are represented by dashed lines identified by reference numerals 114 and 116. Similarly, a heating unit 118 may be formed adjacent container 12 to maintain the contents of container 12 at or near body temperature. Appropriate heat/temperature limits may be incorporated in heating units 114, 116 and 118.

It is to be understood that the respective saline container or sleeve and piston units may have a capacity equivalent to that of blood product container 12 with the admixture to be performed at valve 42 or in container 12. Alternatively, container 14, units 82, 100 may each have a capacity which is a multiple of the capacity of container 12 to permit development of an admixture in each of several blood products containers before refill or replacement of container 14, units 82, 100.

In operation and assuming that container 12 has a substantial free volume, the transfer from container 14, unit 82 or 100 to container 12 is the expressing of saline solution into the container. Subsequent mixing within the container may be effected by alternate inflation/deflation of air bags 52, 54. Final expression of the admixture from container 12 may be effected through valve 42 into conduit 40. It is to be understood that other procedural variations may exist for effecting rapid, forced and mechanical mixing of the blood products and the saline solution.

Several alternative procedures for agitating the admixture may be undertaken. In example, the admixture within container 12 may be drawn into unit 82 through a combination of retraction of plunger 90 and inflation of air bags 52, 54 acting to compress container 12 while valve 42 is in the position depicted in FIG. 5a. At or some point, the movement of plunger 90 may be reversed to force piston 88 to express the admixture through tubes 34 and 20 into container 12. This cycle may be repeated one or more times before the resulting admixture is discharged via valve 42 through conduit 40.

While the principles of the invention have now been made clear an illustrative embodiment, there will be immediately obvious to those skilled in the art many modifications of structure, arrangement, proportions, elements, materials and components, used in the practice of the invention which are particularly adapted for specific environment and operating requirements without departing from those principles.

I claim:

1. A method for warming chilled erythrocytes to prevent hypothermia upon transfusion and to prevent hemolysis during warming, said method comprising the steps of:
   (a) admixing a quantity of the erythrocytes with a quantity of saline solution having a temperature in excess of 45° C.; and
   (b) conveying the admixture to a point of use.

2. The method as set forth in claim 1 wherein said step of admixing includes the step of agitating the admixture.

3. The method as set forth in claim 2 wherein said agitating step is initiated upon initiation of said admixing step.

4. The method as set forth in claim 3 wherein said step of admixing includes the step of admixing equal quantities of the erythrocytes and the saline solution.

5. The method as set forth in claim 1 wherein said step of admixing includes the step of admixing equal quantities of the erythrocyte and saline solution.

6. A method for warming stored blood products having a temperature in the range of 4°–10° C. to a temperature in the range of 32° C. to 39° C. without significant hemolysis, said method comprising the steps of:
(a) admixing a quantity of the blood products with a quantity of saline solution having a temperature in the range of more than 45° C. to less than 80° C.; and
(b) conveying the admixture to a point of use.

7. The method as set forth in claim 6 wherein said admixing step includes the step of dispersing one of the quantities of blood products or saline solution throughout the other.

8. The method as set forth in claim 7 including the step of agitating the quantity of blood products or saline solution within which the other is dispersed.

9. The method as set forth in claim 6 wherein said admixing step includes the step of conveying a flow of each of the quantities of blood products and saline solution to an intersection.

10. The method as set forth in claim 9 wherein said step of conveying includes the steps of conveying at equal flow rates the blood products and the saline solution.

11. The method as set forth in claim 6 including a first container for the blood products and a second container for the saline solution and further including the step of expressing the blood products from the first container and the further step of expressing the saline solution from the second container.

12. The method as set forth in claim 11 wherein said step of expressing and said further step of expressing are exercised simultaneous with said step of admixing.

13. The method as set forth in claim 16 including the step of applying heat to the saline solution within the second container.

14. Apparatus for warming chilled blood products, said apparatus comprising in combination;
(a) means for containing a quantity of the chilled blood products;
(b) a saline solution heated to a temperature in the range of more than 45° C. to less than 80° C.;
(c) means for housing said saline solution; and
(d) means for admixing the blood products and said saline solution to provide an admixture having a temperature in the range of 32° C. to 39° C.

15. The apparatus as set forth in claim 14 including means associated with said housing means for supplying heat to said saline solution.

16. The apparatus as set forth in claim 14 including first means for expressing the blood products from said containing mean and second means for expressing said saline solution from said housing means.

17. The apparatus as set forth in claim 14 wherein said admixing means includes first means for conveying the blood products from said containing means and second means for conveying said saline solution from said housing means and means for interconnecting said first and second conveying means to develop an admixture having a temperature in the range of 32° C. to 39° C.

18. The apparatus as set forth in claim 17 including first means for expressing the blood products from said containing means and second means for expressing said saline solution from said housing means.

19. The apparatus as set forth in claim 14 including means associated with said containing means for supplying heat to the admixture.

20. The apparatus as set forth in claim 14 including means for conveying said saline solution into said containing means.

21. The apparatus as set forth in claim 20 wherein said admixing means includes means for agitating the blood products and said saline solution within said containing means to develop the admixture.

22. The apparatus as set forth in claim 21 including means for expressing the admixture from said containing means.

23. Apparatus for admixing chilled blood products with a heated saline solution, said apparatus comprising in combination:
(a) a first container for chilled blood products at a temperature in the range of 4° C. to 10° C.;
(b) a second container for heated saline solution at a temperature in the range of more than 45° C. to less than 80° C.;
(c) means for admixing the blood products and the saline solution to provide an admixture having a temperature in the range of 32° C. to 39° C.; and
(d) means for conveying the admixture to a point of use.

24. The apparatus as set forth in claim 23 wherein said admixing means includes means for merging the blood products and the saline solution and means for agitating the admixture during at least the merging of the blood products and the saline solution.

25. The apparatus as set forth in claim 24 wherein said merging means includes means for expressing at least one of said first and second containers.

26. The apparatus as set forth in claim 25 wherein the expressed one of said first and second containers is a bag.

27. The apparatus as set forth in claim 24 wherein said agitating means comprises a repetitively inflatable and deflatable air bag.

28. The apparatus as set forth in claim 25 wherein said expressing means comprises a repetitively inflatable and deflatable air bag.

29. The apparatus as set forth in claim 28 wherein said agitating means comprises a repetitively inflatable and deflatable air bag.

30. The apparatus as set forth in claim 23 wherein said admixing means produces the admixture at the rate of at least 250 ml/minute.

31. Apparatus for rapidly warming chilled and stored erythrocytes from a temperature in the range of 4° C. to 10° C. to a temperature in the range of 32° C. to 39° C. without hemolysis, said apparatus comprising in combination:
(a) a first container for containing a quantity of the erythrocytes;
(b) a quantity of heated saline solution at a temperature in the range of 50° C. to less than 80° C.;
(c) a second container for said saline solution;
(d) mean for admixing the erythrocytes and said saline solution to effect a heat transfer from said saline solution to the erythrocytes; and (e) means for conveying the admixture to a point of use.

32. The apparatus as set forth in claim 31 including first means for evacuating said first container and second means for evacuating said second container.

33. The apparatus as set forth in claim 32 wherein each of said first and second evacuating means comprises means for pressurizing the contents of each of said first and second containers, respectively.

34. The apparatus as set forth in claim 33 wherein said pressurizing means includes means for periodically applying pressure to consecutively different locations upon one of said first and second containers.

35. The apparatus as set forth in claim 31 wherein said admixing means includes means for developing the admixture at a rate greater than 500 ml/minute.

36. The apparatus as set forth in claim 31 wherein said first and second containers include equal quantities of erythrocytes and said saline solution, respectively.

37. The apparatus as set forth in claim 31 including means for transferring heat to said saline solution disposed in said second container.

38. The apparatus as set forth in claim 31 including means for transferring heat to the contents of said first container.

* * * * *

UNITED STATES PATENT AND TRADEMARK OFFICE
CERTIFICATE OF CORRECTION

PATENT NO. : 4,808,159

DATED : February 28, 1989

INVENTOR(S) : Ethan B. Wilson

It is certified that error appears in the above-identified patent and that said Letters Patent is hereby corrected as shown below:

```
Col. 1, line 24, "gates" should read --rates--.
Col. 4, line 56, "seconds" should read --seconds;--.
Col. 7, line 10, "ma" should read --may--.
Col. 7, line 27, "it" should read --It--.
```

Signed and Sealed this

Eighteenth Day of July, 1989

Attest:

DONALD J. QUIGG

Attesting Officer

Commissioner of Patents and Trademarks